(12) United States Patent
Giovanniello

(10) Patent No.: US 9,775,345 B2
(45) Date of Patent: Oct. 3, 2017

(54) ANTIMICROBIAL SANITIZER COMPOSITIONS AND METHODS OF MAKING THE SAME

(71) Applicant: SANIT TECHNOLOGIES LLC, Sarasota, FL (US)

(72) Inventor: Joseph Giovanniello, Wayne, NJ (US)

(73) Assignee: Sanit Technologies LLC, Sarasota, FL (US)

( * ) Notice: Subject to any disclaimer, the term of this patent is extended or adjusted under 35 U.S.C. 154(b) by 0 days.

(21) Appl. No.: 14/910,331

(22) PCT Filed: Aug. 7, 2014

(86) PCT No.: PCT/US2014/050183
§ 371 (c)(1),
(2) Date: Feb. 5, 2016

(87) PCT Pub. No.: WO2015/021301
PCT Pub. Date: Feb. 12, 2015

(65) Prior Publication Data
US 2016/0192648 A1 Jul. 7, 2016

Related U.S. Application Data

(60) Provisional application No. 61/862,990, filed on Aug. 7, 2013.

(51) Int. Cl.
| | | |
|---|---|---|
| *A61K 31/14* | (2006.01) | |
| *A01N 33/12* | (2006.01) | |
| *A61Q 17/00* | (2006.01) | |
| *A61K 8/39* | (2006.01) | |
| *A61K 8/41* | (2006.01) | |
| *A61K 8/92* | (2006.01) | |

(52) U.S. Cl.
CPC .............. *A01N 33/12* (2013.01); *A61K 8/39* (2013.01); *A61K 8/416* (2013.01); *A61K 8/922* (2013.01); *A61Q 17/005* (2013.01); *A61K 2800/30* (2013.01)

(58) Field of Classification Search
USPC ............................................... 514/643
See application file for complete search history.

(56) References Cited

U.S. PATENT DOCUMENTS

| | | | |
|---|---|---|---|
| 7,666,824 B2 | 2/2010 | Krzysik et al. | |
| 7,754,770 B2 * | 7/2010 | Curtis | A61K 8/046 514/643 |
| 8,158,163 B2 | 4/2012 | Willimann et al. | |
| 2012/0014896 A1 | 1/2012 | Dombeck | |

FOREIGN PATENT DOCUMENTS

| | | |
|---|---|---|
| WO | 2011103440 A1 | 8/2011 |
| WO | 2013064315 A1 | 5/2013 |

OTHER PUBLICATIONS

Verallo-Rowell, V.M., et al. "Novel Antibacterial and Emollient Effects of Coconut and Virgin Olive Oils in Adult Atopic Dermatitis", Dermatitis, Nov. 1, 2008, pp. 308-315, vol. 19, No. 6, ResearchGate, XP055324840.

* cited by examiner

*Primary Examiner* — Rei-Tsang Shiao
(74) *Attorney, Agent, or Firm* — Coats and Bennett PLLC

(57) ABSTRACT

This disclosure relates to anti-microbial sanitizer compositions and methods of making the same. The sanitizer compositions described herein are comprised of benzalkonium chloride, coconut oil, palm kernel oil, water, dihydroxypropyl PEG-5, linoleammonium chloride, and glycereth-2 cocoate. To forming the sanitizer compositions discussed herein, water is mixed with benzalkonium chloride to form a first mixture. This first mixture is then mixed with coconut oil and palm kernel oil to form a second mixture, which is subsequently heated to at least 100° F. After heating, the second mixture is mixed with dihydroxypropyl PEG-5 to form a third mixture, which is then settled while the temperature is maintained at or above 100° F., Thereafter, the third mixture is cooled to room temperature, and mixed with linoleammonium chloride and glycereth-2 cocoate to form the sanitizer composition.

14 Claims, 2 Drawing Sheets

ANTIMICROBIAL SANITIZER COMPOSITIONS AND METHODS OF MAKING THE SAME

This application is a U.S. National Stage Application of PCT Application No. PCT/US2014/050183, with an international filing date of 7 Aug. 2014. The subject matter of this application is incorporated herein.

BACKGROUND

Hand and skin sanitizers are popular products used to supplement personal hygiene and prevent the spread of bacteria and viruses. Because these sanitizers do not need to be washed from the skin, they are highly convenient and may be used in numerous locations where soap and water are not practical or obtainable.

Traditional sanitizers are alcohol-based. Although alcohol based sanitizers are effective in killing bacteria and viruses, they come with numerous drawbacks. Alcohol-based sanitizers dehydrate the skin and remove lipids and sebum from the skin. This may lead to an increased risk of infection. For example, dehydrated skin may crack and bleed, allowing an infection direct access to the blood stream. The side effects of alcohol-based sanitizer may be worsened by frequent use of the same, use in winter months, and use by those with sensitive skin. The alcohol used in sanitizers is also flammable and has been tied to incidents of flash fire. Alcohol-based sanitizers suffer further drawbacks, as they provide only a short time period of protection and are often ineffective once they dry.

There is a need for a non-alcohol-based sanitizer that eliminates or reduces the threats caused by bacteria and viruses, but does not cause dry skin or flash fire.

SUMMARY

One aspect of the instant application relates to a sanitizer composition comprising benzalkonium chloride, coconut oil, palm kernel oil, water, dihydroxypropyl PEG-5, linoleammonium chloride, and glycereth-2 cocoate.

Another aspect of the instant application relates to forming a sanitizer composition. In one embodiment, water is directed to a tank and mixed with benzalkonium chloride to form a first mixture. This first mixture is then mixed with coconut oil and palm kernel oil to form a second mixture, which is subsequently heated to at least 100° F. After heating, the second mixture is mixed with dihydroxypropyl PEG-5 to form a third mixture. The third mixture is settled while the temperature is maintained at or above 100° F. Thereafter, the third mixture is cooled to room temperature. The third mixture is then mixed with linoleammonium chloride and then with glycereth-2 cocoate to form the sanitizer composition.

In another embodiment, a sanitizer composition is formed by determining the amount of benzalkonium chloride, water, palm kernel oil, coconut oil, dihydroxypropyl PEG-5, linoleammonium chloride, and glycereth-2 cocoate necessary to make a sanitizer composition such that the sanitizer composition comprises 1.0% benzalkonium chloride, 0.30% coconut oil, 0.20% palm kernel oil. 98.67% water, 0.050% dihydroxypropyl PEG-5, 0.020% linoleammonium chloride, and 0.030% glycereth-2 cocoate by weight percent. The determined amount of water is directed to a tank. The tank includes a high speed shear mixer capable of shearing particles such that the average particle diameter after mixing is less than or equal to 1 micron. The water is then mixed with the determined amount of benzalkonium chloride for at least five minutes to form a first mixture. Thereafter, the first mixture is mixed with the determined amount of palm kernel oil and the determined amount of coconut oil for at least thirty minutes to form a second mixture. The second mixture is then heated to at least 100° F. The second mixture is mixed with the determined amount of dihydroxypropyl PEG-5 to form a third mixture, which is then settled for one hour while the temperature is maintained at or above 100° F. Thereafter, the temperature of the third mixture is reduced to room temperature. Settling continues for twenty four hours. Thereafter, the determined amount of linoleammonium chloride is mixed to the third mixture for at least thirty minutes to form a fourth mixture. The fourth mixture is mixed with the determined amount of glycereth-2 cocoate to form the sanitizer composition.

DETAILED DESCRIPTION

Figure 1:
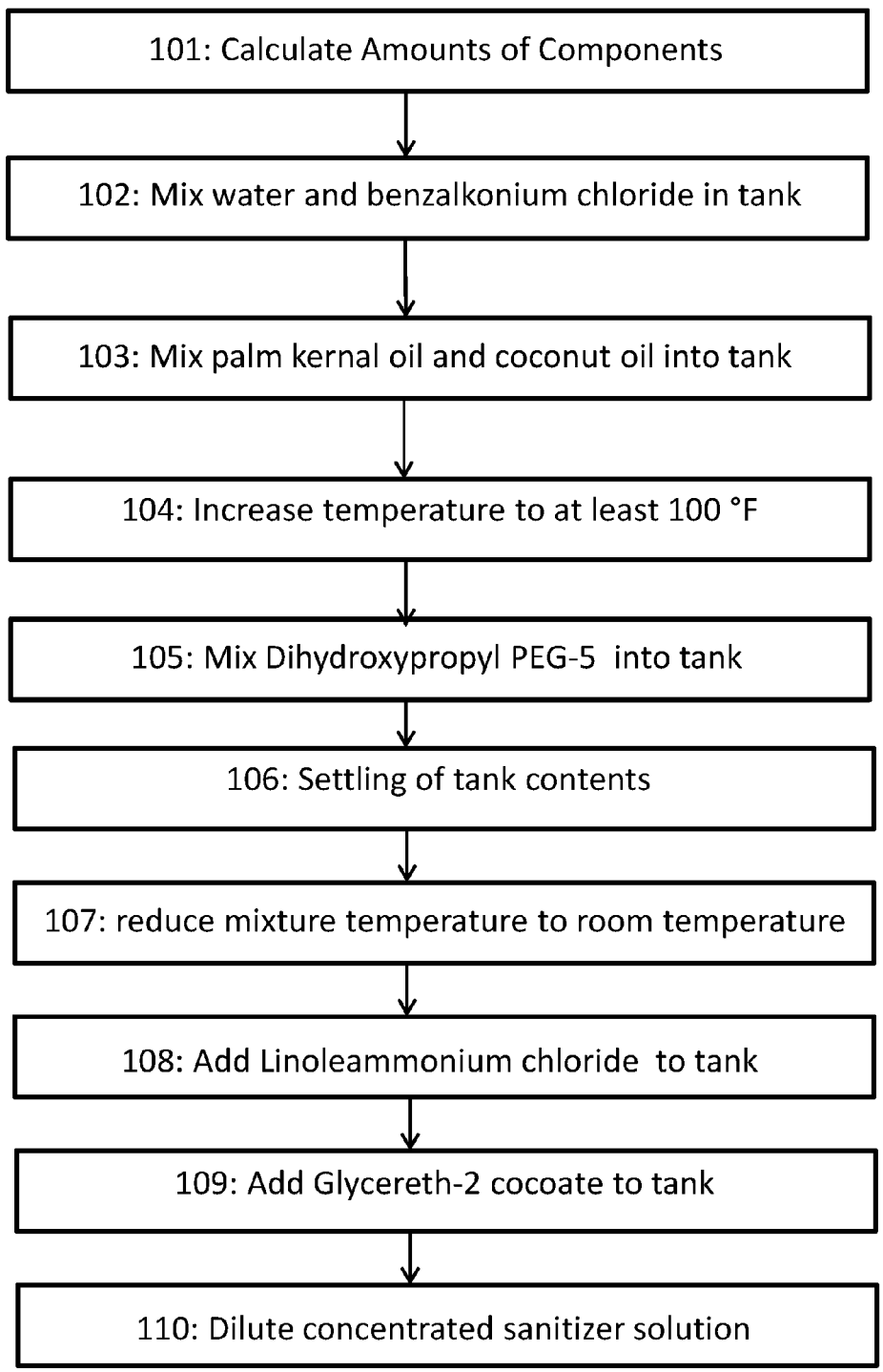
FIG. 1 depicts a flow chart of the steps of one embodiment of the methods described herein.

A sanitizer composition is comprised of benzalkonium chloride and water. In some embodiments, the water is deionized water. Benzalkonium chloride comprises approximately 0.100-0.130 g/lb of the composition. As used herein, "g/b" refers to the grams of the component per pound of the resultant composition, and the term "approximately" means+/−0.001 g/lb.

In some embodiments, the composition may further include glycereth-2 cocoate, dihydroxypropyl PEG-5, other PEGs, linoleammonium chloride, and combinations thereof. By way of example, the composition may include approximately 0.005 g/lb dihydroxypropyl PEG-5. There may be approximately 0.002 g/lb linoleammonium chloride in the composition. The composition may further include approximately 0.003 g/b glycereth-2 cocoate.

Embodiments of the sanitizer composition further include natural oils. Natural oils may aid in preventing side effects of traditional sanitizer solutions, such as dry skin. Natural oils that may be used with the compositions described herein include, but are not limited to, coconut oil, palm kernel oil, and combinations thereof. Some embodiments may comprise approximately 0.003 g/lb coconut oil. The composition may further include 0.020 g/lb palm kernel oil. One exemplar sanitizer composition may be as follows:

TABLE ONE

Components of Sanitizer Composition

| Component | Amount Present (g/lb) |
|---|---|
| Benzalkonium chloride | 0.100-0.130 |
| Coconut oil | 0.003 |
| Palm kernel oil | 0.020 |
| Water | 0.837-0.867 |
| Dihydroxypropyl PEG-5 | 0.005 |
| Linoleammonium chloride | 0.002 |
| Glycereth-2 cocoate | 0.003 |

In some embodiments, the sanitizer may be concentrated. Concentrated sanitizer may include the components of the sanitizer discussed above. In the concentrated sanitizer, however, included components would be present in higher concentrations. Because the FDA monograph for benzalkonium chloride requires the percentage of benzalkonium chloride to be between 0.10% and 0.13%, the concentrated solution should be appropriately diluted so that the benzalkonium chloride concentration of the diluted sanitizer falls within the monograph.

By way of example a concentrated sanitizer may comprise the following:

TABLE 2

Components of Concentrated Sanitizer Composition

| Component | Amount Present (weight %) |
|---|---|
| Benzalkonium chloride | 1.0% |
| Coconut oil | 0.030% |
| Palm kernel oil | 0.20% |
| Water | 98.67% |
| Dihydroxypropyl PEG-5 | 0.050% |
| Linoleammonium chloride | 0.020% |
| Glycereth-2 cocoate | 0.030% |

In this example, the concentrated sanitizer is ten times more concentrated than the sanitizer solution disclosed above. In order to use this example concentrated sanitizer on human skin, the concentrated sanitizer should be diluted 1 to 10 (resulting in, for example, 0.10 weight percent of benzalkonium chloride). Although the sanitizer shown in this example is ten times more concentrated, one of ordinary skill in the art appreciates that concentrated sanitizer may be more or less concentrated than this example.

The sanitizers described herein may be made using the novel methods described herein. Indeed, testing has shown that manufacturing the sanitizers using these methods increases the ability of the sanitizers to kill bacteria, viruses, and other harmful organisms.

FIG. 1 depicts a flow chart showing the steps of one embodiment of the methods for making the sanitizers disclosed herein. In some embodiments, the sanitizer is made by making the concentrated sanitizer solution disclosed in Table 2, above, and then diluting that solution to safe, appropriate levels, such as, for example, the sanitizer solution shown in Table 1. One of skill in the art appreciates that the Table 2 and Table 1 values discussed herein are exemplars and that other sanitizer solutions of varying benzalkonium chloride concentrations may be formed utilizing the methods described herein.

The amounts of each component to be added may be determined (101). Because the amounts of each component are dependent on the size of the batch to be prepared, these amounts are calculated using the weight percentages shown in Table 2 for a particular batch. In some instances, the amount of water to be held in the vessel being utilized in these methods may be determinative of the amount of water to be used, that is, the amounts of the other components may be determined based on their relation, in weight percent, to the amount of water being held in the vessel. Although in some embodiments, the amounts of all components may be calculated prior to the first components being added together, one of skill in the art appreciates that the appropriate amount of a given ingredient may be calculated at any time prior to the inclusion of that ingredient into the concentrated sanitizer solution.

Figure 2:
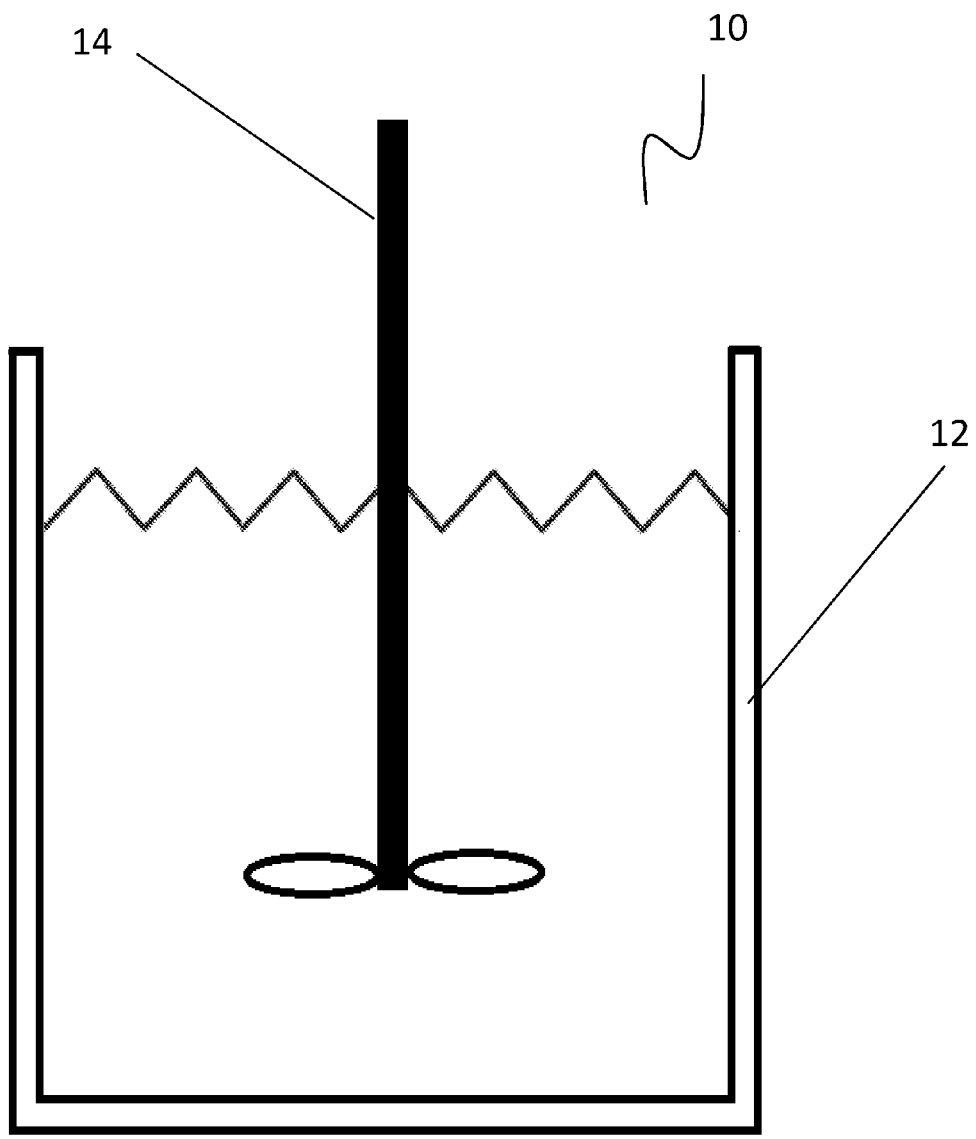
FIG. 2 depicts a schematic of an apparatus which may be utilized to practice the methods described herein.

FIG. 2 depicts an exemplar apparatus that may be used with the methods described herein. The concentrated sanitizer solution (see Table 2) may be prepared in a mixing tank 10. A heat source may be applied to mixing tank 10. Any source appropriate for heating a tank or other liquid-containing vessel may be utilized. In some embodiments, mixing tank 10 is a heated jacket style tank, and includes a heating jacket 12 as the heat source. Mixing tank 10 further includes a mixer 14. Mixer 14 is a high speed mixer and, in some embodiments, includes a speed control. Mixer 14 may be any style mixer that allows particle sizes of components to be reduced to at least as small as 1 micron in diameter. In a preferred embodiment, mixer 14 is a shear style mixer. The mixer may be used with a baffle plate. One such mixer that may be utilized for mixer 14 is a Hill type mixer.

Water is placed into mixing tank 10. In some embodiments, the water is at room temperature. The benzalkonium chloride is added to the water and mixed using mixer 14 for approximately five (5) minutes (102). It is noted that longer mixing times may be utilized. The mixing reduces the average particle size of the benzalkonium chloride to at least as small as 1 micron. In some embodiments, the mixing reduces the particle size of the benzalkonium chloride to sizes on the nanometer scale.

By varying the degree of the blade in the mixer, one may control the size of the particle. For example, if a particle size of 1 micron is desired, the blade should be set at 45 degrees. By way of another example, a blade set at 15 degrees results in a particle size of 0.05 microns.

Mixing time may be dependent on the amount of a mixing vortex created by the mixer. The mixers identified above create these vortexes, which aid in grinding particles and decreasing the particle size. An increase in the speed of the mixer increases the amount of vortex generated and decreases the time to grind the particles. For example, in some embodiments using the Hill mixers described herein, mixing may occur using a rear stat to control the speed to between 2500 rpm mixing and 10,000 rpm.

After mixing the water with the benzalkonium chloride, the palm kernel oil and coconut oil are slowly added to mixing tank 10 (103). In one embodiment, the palm kernel oil and coconut oil are added and mixed over a period of approximately thirty (30) minutes. The average particle sizes of the palm kernel oil and coconut oil are also reduced to at least 1 micron, and preferably to sizes on the nanometer scale. These reduced particle sizes allow the particles of benzalkonium chloride to couple with the particles of palm kernel oil and coconut oil. While some embodiments may add palm kernel oil and coconut oil simultaneously, one of skill in the art appreciates these oils may be added at the same time, or in two successive mixing periods (i.e., palm kernel oil is added and mixed for thirty minutes, then coconut oil is added and mixed for thirty minutes, or, conversely, coconut oil is added and mixed for thirty minutes, then palm kernel oil is added and mixed for thirty minutes). One of skill in the art further appreciates that longer mixing times may be utilized.

After mixing the palm kernel oil and coconut oil into mixing tank 10, the temperature of the contents of mixing tank 10 is increased to at least 100° F., or more preferably to a temperature between 120° F. and 130° F. (104). Any standard temperature probe or other standard device for measuring temperature may be utilized to determine the temperature of the contents of mixing tank 10. The increase in temperature may occur while mixing with mixer 14.

Thereafter, Dihydroxypropyl PEG-5 is slowly added to mixing tank 10 (105). In some embodiments, Dihydroxypropyl PEG-5 may be added and mixed with the contents of mixing tank 10 over a period of approximately thirty minutes. One of skill in the art appreciates that longer mixing times may be utilized.

While maintaining the temperature at or above 100° F., the mixture in mixing tank 10 is allowed to settle (106). Settling may occur by cessation of mixing with mixer 14. Appropriate times for settling may be approximately one (1) hour. In some embodiments, settling may occur for a longer period of time.

After settling, the temperature of the mixture in mixing tank 10 is reduced to room temperature (107). Room temperature is generally considered to be temperatures between 68° F. and 78° F. In some preferred embodiments, this cooling period may be a period of cooling and additional settling that lasts approximately twenty four (24) hours.

When the temperature of the mixture in mixing tank 10 reaches room temperature, Linoleammonium chloride is slowly added to mixing tank 10 (108). In some embodiments, Linoleammonium chloride is added to mixing tank 10 over a period of approximately thirty minutes. The Linoleammonium chloride may be mixed with the contents of mixing tank 10 via mixer 14.

Thereafter, Glycereth-2 cocoate may be mixed into mixing tank 10 to form the concentrated sanitizer solution (109). In some embodiments, Glycereth-2 cocoate is mixed with the contents of mixing tank 10 via mixer 14.

The concentrated sanitizer solution may be provided to entities that desire a concentrated solution or which desire to perform their own dilution prior to use. In the alternative, the concentrated sanitizer solution may be diluted as part of the instant methods. In such situations, water is added to the concentrated sanitizer solution such that the weight percentage of the benzalkonium chloride in solution is approximately 0.10% (110). The diluted sanitizer comprises approximately the component amounts shown in Table 1. Dilution may be performed by, for example, transferring a fraction of the concentrated sanitizer solution to another vessel and adding a calculated amount of water such that the diluted sanitizer comprises approximately 0.10% benzalkonium chloride by weight percent. In other embodiments, if space permits, water may be added directly to the vessel to dilute the concentrated sanitizer solution to a desired strength.

Laboratory tests were performed using the sanitizer disclosed in Table 1 above. It was discovered that the sanitizers disclosed herein are highly effective in killing bacteria, viruses, and other harmful microorganisms. This high efficiency is brought about, at least in part, due to the novel particle size reduction and resultant coupling described above.

The Table 1 sanitizer was tested to determine its efficiency at reducing bacteria on the skin via a chlorine equivalence test. Samples were prepared of *Staphylococcus aureus* ATCC 6538 ($7.6 \times 10^8$ colony forming units per mL of text mixture) and *Salmonella typhi* ATCC 6539 ($1.2 \times 10^8$ colony forming units per mL of text mixture). The samples were then treated against a NaOCl control at 200 ppm, 100 ppm, and 50 ppm, as well as the sanitizer disclosed herein. Thereafter, ten subculture series were taken. The sanitizer disclosed herein showed no growth of organisms (0) for each subculture series. Each of the NaOCl control series eventually showed growth of organisms (+). Table 3, below, discloses these results.

TABLE 3

Results of Chlorine Equivalence Test showing growth of organism (+) or no growth of organism (0) for each subculture series. Subcultures of positive broths (tubes showing growth) demonstrated pure cultures of test organism.

| Organism | Substance Tested | Concentration | Subculture Series | | | | | | | | | |
|---|---|---|---|---|---|---|---|---|---|---|---|---|
| | | | 1 | 2 | 3 | 4 | 5 | 6 | 7 | 8 | 9 | 10 |
| *Staphylococcus aureus* | NaOCl | 200 pm | 0 | 0 | 0 | 0 | 0 | + | + | + | + | + |
| | | 100 ppm | 0 | 0 | + | + | + | + | + | + | + | + |
| | | 50 ppm | 0 | + | + | + | + | + | + | + | + | + |
| | Sanitizer | See Table 1 | 0 | 0 | 0 | 0 | 0 | 0 | 0 | 0 | 0 | 0 |
| *Salmonella typhi* | NaOCl | 200 ppm | 0 | 0 | 0 | 0 | 0 | 0 | + | + | + | + |
| | | 100 ppm | 0 | 0 | 0 | + | + | + | + | + | + | + |
| | | 50 ppm | 0 | 0 | + | + | + | + | + | + | + | + |
| | Sanitizer | See Table 1 | 0 | 0 | 0 | 0 | 0 | 0 | 0 | 0 | 0 | 0 |

The sanitizer disclosed in Table 1 was further tested via a time kill assay. This time kill assay was performed utilizing the standards and procedures set out by the American Society for Testing and Materials in E2315-03, Guide for Assessment of Microbial Activity Using a Time-Kill Procedure, Volume 11.05, Copyright 2005.

The results of these tests are shown in Table 4, below. These results demonstrate that the sanitizer compositions described herein are effective antimicrobials against both Gram-Positive and Gram-negative bacterial pathogens.

TABLE 4

Results from Time-Kill Assay. Data listed is from an exposure time of 15 Seconds.

| Organism | Test Population Control (CFU/ml) | Number of Survivors (CFU/ml) | % Reduction | Log Reduction |
|---|---|---|---|---|
| *Campylobacter jejuni* ATCC 29428 | $1.02 \times 10^7$ | $<1 \times 10^2$ | >99.999 | >5.00 $Log_{10}$ |
| *Candida albicans* ATCC 10231 | $1.60 \times 10^5$ | $6.0 \times 10^3$ | 96.3 | 1.42 $Log_{10}$ |
| *Clostridium difficile* ATCC 9689 | $3.40 \times 10^6$ | <2 | >99.9999 | >6.30 $Log_{10}$ |
| *Enterococcus faecalis* Vancomycin Resistant (VRE) ATCC 51575 | $1.12 \times 10^6$ | $3.2 \times 10^1$ | 99.99 | 4.54 $Log_{10}$ |
| *Escherichia coli* ATCC 11229 | $3.80 \times 10^6$ | 4 | 99.999 | 6.00 $Log_{10}$ |
| *Escherichia coli* O157:H7 ATCC 35150 | $1.26 \times 10^6$ | <2 | >99.999 | >5.80 $Log_{10}$ |
| *Klebsiella pneumoniae* ATCC 4352 | $1.10 \times 10^6$ | 2 | 99.999 | 5.70 $Log_{10}$ |

TABLE 4-continued

Results from Time-Kill Assay. Data listed is from an exposure time of 15 Seconds.

| Organism | Test Population Control (CFU/ml) | Number of Survivors (CFU/ml) | % Reduction | Log Reduction |
|---|---|---|---|---|
| Klebsiella pneumoniae NDM -1 positive CDC 1000527 ("New Dehli" superstrain) | $7.4 \times 10^5$ | <5 | >99.9999 | >5.2 $Log_{10}$ |
| Listeria monocytogenes ATCC 19117 | $4.7 \times 10^6$ | $1.9 \times 10^1$ | 99.9 | 3.39 $Log_{10}$ |
| Pseudomonas aeruginosa ATCC 15442 | $3.5 \times 10^6$ | <2 | 99.9999 | >6.20 $Log_{10}$ |
| Salmonella choleraesuis serotype enteritidis ATCC 4931 | $6.8 \times 10^5$ | 2 | >99.999 | 5.50 $Log_{10}$ |
| Salmonella choleraesuis serotype paratyphi ATCC 8759 | $5.6 \times 10^5$ | <2 | >99.999 | >5.50 $Log_{10}$ |
| Salmonella choleraesuis serotype pullorum ATCC 19945 | $8.9 \times 10^5$ | <2 | >99.999 | >5.70 $Log_{10}$ |
| Salmonella choleraesuis serotype typhimurium ATCC 23564 | $7.7 \times 10^5$ | 6 | >99.999 | >5.10 $Log_{10}$ |
| Salmonella typhi ATCC 6539 | $1.26 \times 10^6$ | 2 | 99.999 | 5.80 $Log_{10}$ |
| Shigella dysenteriae ATCC 13313 | $1.3 \times 10^6$ | <2 | >99.999 | >5.80 $Log_{10}$ |
| Shigella flexneri ATC 12022 | $1.39 \times 10^6$ | $2.8 \times 10^1$ | 99.99 | 4.69 $Log_{10}$ |
| Shigella sonnei ATCC 25931 | $2.43 \times 10^7$ | $2.0 \times 10^1$ | 99.9999 | 6.09 $Log_{10}$ |
| Staphylococcus aureus ATC 6538 | $6.7 \times 10^6$ | <2 | >99.9999 | >6.53 $Log_{10}$ |
| Staphylococcus aureus Methicillin Resistant (MRSA) ATCC 33592 | $1.23 \times 10^7$ | $3.8 \times 10^3$ | >99.9 | 3.51 $Log_{10}$ |
| Staphylococcus aureus Community Associated Methicillin Resistant (MRSA) NARSA NRS 123, Genotype USA400 | $1.18 \times 10^6$ | $5.8 \times 10^2$ | >99.9 | >3.03 $Log_{10}$ |
| Staphlyococcus epidermidis ATCC 12228 | $7.2 \times 10^5$ | <2 | 99.999 | 5.56 $Log_{10}$ |
| Streptococcus pneumonia ATCC 6305 | $6.4 \times 10^5$ | <2 | >99.999 | >5.51 $Log_{10}$ |
| Streptococcus pyogenes ATCC 19615 | $1.77 \times 10^6$ | <2 | >99.999 | >5.90 $Log_{10}$ |
| Vibrio cholera ATCC 11623 | $4.7 \times 10^5$ | <2 | >99.999 | >5.40 $Log_{10}$ |
| Xanthomonas axonopodis (Citrus Canker) ATCC 49118 | $1.28 \times 10^6$ | $3.6 \times 10^1$ | >99.99 | 4.55 $Log_{10}$ |
| Yersinia enterocolitica ATCC 23715 | $2.23 \times 10^6$ | $3.8 \times 10^1$ | 99.99 | 4.77 $Log_{10}$ |

Although the present composition has been shown and described in considerable detail with respect to only a few/particular exemplary embodiments thereof, it should be understood by those skilled in the art that it is not intended to limit the composition to the embodiments since various modifications, omissions, and additions may be made to the disclosed embodiments without materially departing from the novel teachings and advantages of the composition, particularly in light of the foregoing teachings.

What is claimed is:

1. A method of making a sanitizer composition, comprising:
   directing water to a tank;
   mixing benzalkonium chloride with the water in the tank to form a first mixture;
   mixing coconut oil and palm kernel oil with the first mixture to form a second mixture;
   heating the second mixture to at least 100° F.;
   after heating the second mixture, mixing dihydroxypropyl PEG-5 with the second mixture to form a third mixture;
   settling the third while maintaining the temperature at or above 100° F.;
   after settling the third mixture, cooling the third mixture to room temperature;
   mixing linoleammonium chloride to the third mixture to form a fourth mixture; and
   mixing glycereth-2 cocoate to the fourth mixture to form a sanitizer composition.

2. The method of claim 1, further comprising determining the amount of benzalkonium chloride, water, palm kernel oil, coconut oil, dihydroxypropyl PEG-5, linoleammonium chloride, and glycereth-2 cocoate necessary to make a sanitizer composition wherein the sanitizer composition comprises 1.0% benzalkonium chloride, 0.30% coconut oil, 0.20% palm kernel oil, 98.67% water, 0.050% dihydroxypropyl PEG-5, 0.020% linoleammonium chloride, and 0.030% glycereth-2 cocoate by weight percent.

3. The method of claim 1, wherein the tank is a heated jacket tank.

4. The method of claim 1, wherein the tank includes a high speed mixer.

5. The method of claim 4, wherein the mixer is a shear mixer.

6. The method of claim 4, wherein the mixer is capable of reducing particle size to particles with an average diameter of 1 micron.

7. The method of claim 1, wherein mixing the benzalkonium chloride with the water occurs for a period of at least five minutes.

8. The method of claim 1, wherein mixing coconut oil and palm kernel oil with the first mixture occurs for a period of 30 minutes.

9. The method of claim 1, wherein the second mixture is heated to a temperature between 120° F. and 130° F.

10. The method of claim 1, wherein cooling the third mixture to room temperature occurs over a period of twenty four hours.

11. The method of claim 1, further comprising diluting the sanitizes composition to form a diluted composition.

12. The method of claim 11, wherein the benzalkonium chloride comprises 0.10 weight percent of the diluted composition.

13. A method of forming a sanitizer composition, the method comprising:
   determining the amount of benzalkonium chloride, water, palm kernel oil, coconut oil, dihydroxypropyl PEG-5, linoleammonium chloride, and glycereth-2 cocoate necessary to make a sanitizer composition wherein the sanitizer composition comprises 1.0% benzalkonium chloride, 0.30% coconut oil, 0.20% palm kernel oil, 98.67% water, 0.050% dihydroxypropyl PEG-5, 0.020% linoleammonium chloride, and 0.030% glycereth-2 cocoate by weight percent;

directing the determined amount of water into a tank, wherein the tank includes a high speed shear mixer, and wherein the mixer is capable of shearing particles such that the average particle diameter after mixing is less than or equal to 1 micron;

mixing the water with the determined amount of benzalkonium chloride for at least five minutes to form a first mixture;

mixing the determined amount of palm kernel oil and the determined amount of coconut oil with the first mixture for at least thirty minutes to form a second mixture;

heating the second mixture to at least 100° F.;

mixing the determined amount of dihydroxypropyl PEG-5 with the second mixture at a temperature at or above 100° F. to form a third mixture;

settling the third mixture for one hour while maintaining the temperature of the third mixture at or above 100° F.;

reducing the temperature of the third mixture to room temperature while continuing to settle the third mixture for twenty four hours;

mixing the determined amount of linoleammonium chloride with the third mixture for at least thirty minutes to form a fourth mixture; and mixing the determined amount of glycereth-2 cocoate with the fourth mixture to form the sanitizer composition.

14. The method of claim 13, further comprising diluting the sanitizer composition to form a diluted composition such that the benzalkonium chloride comprises 0.10 weight percent of the diluted composition.

\* \* \* \* \*